US008630878B1

(12) United States Patent
Kravets et al.

(10) Patent No.: US 8,630,878 B1
(45) Date of Patent: Jan. 14, 2014

(54) DETERMINING LIKELY OUTCOMES OF ACTIVE INSURANCE CLAIMS BY CALCULATING AND EXAMINING AGGREGATED OUTCOMES OF MATCHING HISTORIC CLAIMS

(75) Inventors: Alexandre Kravets, Woodland Hills, CA (US); Davidson M Pattiz, Woodland Hills, CA (US); Vernon L. Steiner, Woodland Hills, CA (US)

(73) Assignee: Zenith Insurance Company, Woodland Hills, CA (US)

( * ) Notice: Subject to any disclaimer, the term of this patent is extended or adjusted under 35 U.S.C. 154(b) by 6 days.

(21) Appl. No.: 13/163,452

(22) Filed: Jun. 17, 2011

(51) Int. Cl.
*G06Q 40/00* (2012.01)

(52) U.S. Cl.
USPC .................................................. 705/4

(58) Field of Classification Search
USPC .................................................. 705/4
See application file for complete search history.

(56) References Cited

U.S. PATENT DOCUMENTS

| | | | | |
|---|---|---|---|---|
| 5,544,044 | A * | 8/1996 | Leatherman ...................... | 705/3 |
| 5,950,169 | A | 9/1999 | Borghesi et al. | |
| 6,117,073 | A | 9/2000 | Jones et al. | |
| 8,180,789 | B1 * | 5/2012 | Wasserman et al. .......... | 707/766 |
| 2002/0049618 | A1 * | 4/2002 | McClure et al. ................... | 705/4 |
| 2004/0039600 | A1 * | 2/2004 | Kramer et al. .................... | 705/2 |
| 2005/0278196 | A1 * | 12/2005 | Potarazu et al. .................. | 705/2 |
| 2008/0010086 | A1 * | 1/2008 | Skelly et al. ...................... | 705/2 |
| 2009/0157436 | A1 * | 6/2009 | Craycraft .......................... | 705/4 |
| 2011/0071856 | A1 * | 3/2011 | Nasenbenny et al. ............. | 705/4 |
| 2011/0161115 | A1 * | 6/2011 | Hampton .......................... | 705/4 |
| 2011/0320223 | A1 * | 12/2011 | Drennan et al. .................. | 705/4 |
| 2012/0143629 | A1 * | 6/2012 | Bonner et al. .................... | 705/4 |
| 2012/0191478 | A1 * | 7/2012 | Klement .......................... | 705/3 |

OTHER PUBLICATIONS

Non-Final Office Action, dated Jul. 18, 2013, for U.S. Appl. No. 13/163,480, Alexandre Kravets et al., inventors, filed Jun. 17, 2011, entitled "Determining Likely Outcomes of Active Insurance Claims by Examining Sentinel Claim Events."

* cited by examiner

*Primary Examiner* — Elda Milef
(74) *Attorney, Agent, or Firm* — McDermott Will & Emery LLP

(57) ABSTRACT

An insurance claim analysis system may generate information indicative of a possible outcome of an active insurance claim. A historic insurance claim information database may hold historic information about historic insurance claims. A database query module may query the historic insurance claim information database for historic insurance claims that match search criteria indicative of one or more aspects of the active insurance claim. A data aggregation module may calculate an aggregate of an aspect of the historic information about the historic insurance claims that match the search criteria or a subset thereof. A report generation module may generate a report that includes the calculated aggregate of the aspect of the historic information.

20 Claims, 14 Drawing Sheets

| GENERAL | |
|---|---|
| Number | — 201 |
| Name | — 203 |
| Age | — 205 |
| Location | — 207 |
| Sex | — 209 |
| Surgery (y/n) | — 211 |
| Litigation (y/n) | — 213 |
| Permanent Disability (y/n) | — 215 |

| CO-MORBITIES | |
|---|---|
| Mental Disorders (y/n) | — 401 |
| Diabetes (y/n) | — 403 |
| Tobacco (y/n) | — 405 |
| Obesity (y/n) | — 407 |
| Hypertension (y/n) | — 409 |
| Inflammatory Condition (y/n) | — 411 |
| Degenerative Condition (y/n) | — 413 |

| DIAGNOSES | |
|---|---|
| DxCAT | — 301 |
| DiagRank | — 303 |
| DiagCode | — 305 |
| DiagDescr | — 307 |
| DxGroup | — 309 |
| DxSubGroup | — 311 |
| DxBodySystem | — 313 |
| DxLocation | — 315 |
| DxDetail | — 317 |

| DELPHI TOOL | | | | | | | |
|---|---|---|---|---|---|---|---|
| Please Enter Claim No. | 440411 | | | Generate Report | | | |
| Claim No: 440411 | | | | Injured Worker: JANE DOE | | DOI: 10/13/2010 | |
| Wages: $1,245.79 | | | | Job: OCCUPATIONAL THERAPIST | | Status: C (04/29/2011) | |
| TD Rate: $830.53 | | | | Employer: COMPREHENSIVE CARE, INC | | Decision: ACCEPT | |
| Nature of Accident: | | | | | | | |
| Body Parts: LOWER BACK AREA - STRAIN | | | | | | | |
| Diagnosis: | | | | | | | |

| DxCAT | DiagRank | DiagCode | DiagDescr | DxGroup | DxSubGroup | DxBodySystem | DxLocation | DxDetail |
|---|---|---|---|---|---|---|---|---|
| 108030700 | PRIMARY | 847.2 | SPARIN LUMBAR REGION | Trauma | Sprains and strains; traumatic arthropathies; loose bodies in joints, joint effusion | Muscol-skeletal system soft tissue and connective tissue | Back, Inc. thoracic, lumbar, lumbosacaral and misc. areas of spinal column, spinal cord or spinal nerve roots | Misc. or no addl details specified |
| 323080700 | SECONDARY | 722.10 | LUMBAR DISC DISPLACEMENT | Non-infectious conditions | Inflammatory and degenerate disorders, atrophy | Spinal column or intervertabral discs | Back, Inc. thoracic, lumbar, lumbosacaral and misc. areas of spinal column, spinal cord or spinal nerve roots | Misc. or no addl details specified |
| 700030000 | TERTIARY | 728.85 | SPASM OF MUSCLE | Pain, misc. symptoms, ill-defined conditions | Misc. or type not specified | Musculo-skeletal system, soft tissue and connective tissue | Anatoic location not specified or not applicable | Misc. or no addl details specified |

FIG. 6

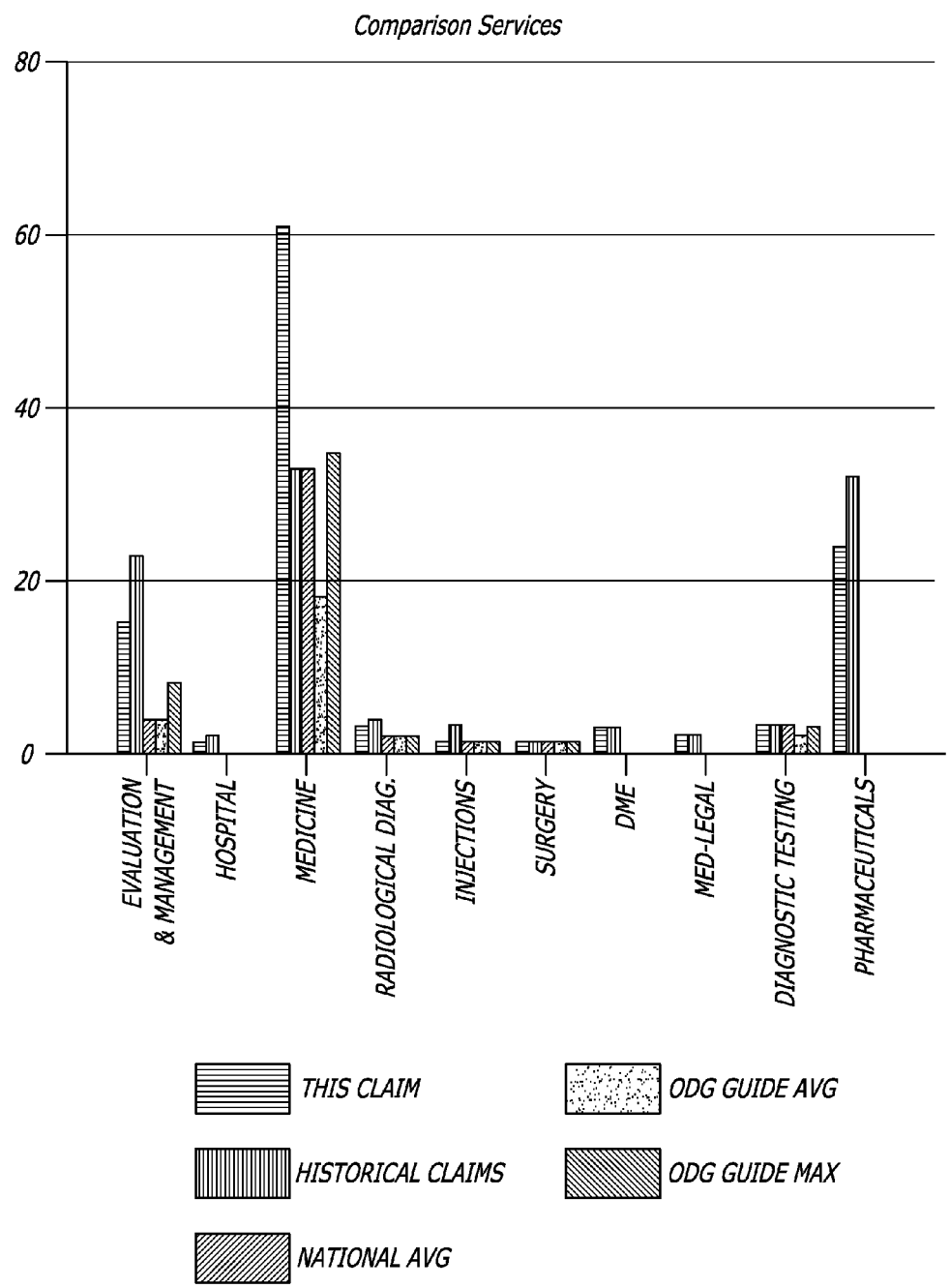

| Medical Services | Procedure | Services | Zenith's Avg Services | Natl. Avg. | ODG Guide Avg | ODG Guide Max |
|---|---|---|---|---|---|---|
| EVALUATION & MANAGEMENT | | 15 | 23 | 4 | 4 | 8 |
| | Emergency Room Visit | 0 | 2 | 1 | 1 | 1 |
| | Office Visit | 6 | 18 | 2 | 2 | 6 |
| | Specialist Consult. | 3 | 1 | 1 | 1 | 1 |
| | Other | 6 | 2 | 0 | 0 | 0 |
| HOSPITAL | | 1 | 2 | 0 | 0 | 0 |
| | Other | 1 | 2 | 0 | 0 | 0 |
| MEDICINE | | 61 | 33 | 33 | 18 | 35 |
| | Chiropractic Treatment | 11 | 15 | 20 | 7 | 17 |
| | Osteopathic Treatment | 0 | 0 | 4 | 6 | 6 |
| | Physical Therapy | 49 | 15 | 8 | 4 | 11 |
| | Other | 1 | 3 | 1 | 1 | 1 |
| RADIOLOGICAL DIAG. | | 3 | 4 | 2 | 2 | 2 |
| | CT Scan | 0 | 1 | 0 | 0 | 0 |
| | MRI | 2 | 1 | 1 | 1 | 1 |
| | Other | 1 | 2 | 1 | 1 | 1 |
| INJECTIONS | | 1 | 3 | 1 | 1 | 1 |
| SURGERY | | 1 | 1 | 1 | 1 | 1 |
| | Minor | 1 | 1 | 1 | 1 | 1 |
| DME | | 3 | 3 | 0 | 0 | 0 |
| MED-LEGAL | | 2 | 2 | 0 | 0 | 0 |
| DIAGNOSTIC TESTING | | 3 | 3 | 3 | 2 | 3 |
| | EMG/NCS | 2 | 1 | 1 | 1 | 1 |
| | Range of Motion/Muscle | 1 | 1 | 2 | 1 | 2 |
| | Sleep Study | 0 | 1 | 0 | 0 | 0 |
| PHARMACEUTICALS | | 24 | 32 | 0 | 0 | 0 |
| | Anti-Convulsants | 0 | 3 | 0 | 0 | 0 |
| | Anti-Inflammatory | 3 | 5 | 0 | 0 | 0 |
| | Compounded Medications | 2 | 0 | 0 | 0 | 0 |
| | Musculoskeletal Therapy | 3 | 6 | 0 | 0 | 0 |
| | Opioids | 7 | 10 | 0 | 0 | 0 |
| | Ulcer Therapy | 7 | 2 | 0 | 0 | 0 |
| | Other | 2 | 6 | 0 | 0 | 0 |

*FIG. 12*

| Medical Services | Procedure | Paid | Zenith's Avg Paid | Natl. Avg Paid |
|---|---|---|---|---|
| EVALUATION & MANAGEMENT | | $815 | $2,180 | $451 |
| | Emergency Room Visit | $0 | $521 | $122 |
| | Office Visit | $458 | $1,113 | $140 |
| | Specialist Consult. | $193 | $372 | $189 |
| | Other | $164 | $174 | $0 |
| HOSPITAL | | $1,124 | $107 | $0 |
| | Other | $1,124 | $107 | $0 |
| MEDICINE | | $4,619 | $1,645 | $1,222 |
| | Chiropractic Treatment | $252 | $458 | $757 |
| | Osteopathic Treatment | $0 | $0 | $137 |
| | Physical Therapy | $4,367 | $860 | $289 |
| | Other | $0 | $327 | $39 |
| RADIOLOGICAL DIAG. | | $0 | $1,579 | $1,061 |
| | CT Scan | $0 | $238 | $0 |
| | MRI | $0 | $1,014 | $957 |
| | Other | $0 | $327 | $104 |
| INJECTIONS | | $301 | $890 | $187 |
| SURGERY | | $65 | $67 | $9 |
| | Minor | $65 | $67 | $9 |
| DME | | $438 | $600 | $0 |
| MED-LEGAL | | $1,156 | $1,554 | $0 |
| DIAGNOSTIC TESTING | | $2,427 | $1,203 | $225 |
| | EMG/NCS | $2,391 | $1,041 | $125 |
| | Range of Motion/Muscle | $36 | $112 | $100 |
| | Sleep Study | $0 | $50 | $0 |
| PHARMACEUTICALS | | $1,643 | $2,883 | $0 |
| | Anti-Convulsants | $0 | $320 | $0 |
| | Anti-Inflammatory | $73 | $359 | $0 |
| | Compounded Medications | $554 | $0 | $0 |
| | Musculoskeletal Therapy | $517 | $793 | $0 |
| | Opioids | $38 | $571 | $0 |
| | Ulcer Therapy | $430 | $394 | $0 |
| | Other | $31 | $446 | $0 |
| | Total: | $12,588 | $12,708 | |

| ODG Guideline | ICD9 Code | Description |
|---|---|---|
| ⊘ | 427.89 | OTHER SPECIFIED CARDIAC DYSRHYTHMIAS |
| ⊘ | 719.46 | PAIN IN JOINT, LOWER LEG |
| ⊘ | 721.3 | LUMBOSACRAL SPONDYLOSIS WITHOUT MYELOPATHY |
| ⊘ | 721.90 | SPONDYLOSIS UNSPEC SITE W/O MENTION MYELOPATHY |
| ⊘ | 722. | INTERVERTEBRAL DISC DISORDERS |
| ⊘ | 722.10 | DISPLCMT LUMBAR INTERVERT DISC W/O MYELOPATHY |
| ⊘ | 722.2 | DISPLCMT INTERVERT DISC SITE UNS W/O MYELOPATHY |
| ⊘ | 722.4 | DEGENERATION OF CERVICAL INTERVERTEBRAL DISC |
| ⊘ | 722.52 | DEGEN LUMBAR/LUMBOSACRAL INTERVERTEBRAL DISC |
| ⊘ | 722.82 | POSTLAMINECTOMY SYNDROME THORACIC REGION |
| ⊘ | 724.1 | PAIN IN THORACIC SPINE |
| ⊘ | 724.2 | LUMBAGO |
| ⊘ | 724.4 | THORACIC/LUMBOSACRAL NEURITIS/RADICULITIS UNSPEC |
| ⊘ | 724.8 | OTHER SYMPTOMS REFERABLE TO BACK |
| ⊘ | 728.85 | SPASM OF MUSCLE |
| ⊘ | 728.9 | UNSPECIFIED DISORDER OF MUSCLE LIGAMENT & FASCIA |
| ⊘ | 729.5 | PAIN IN SOFT TISSUES OF LIMB |
| ⊘ | 780.96 | GENERALIZED PAIN |
| ⊘ | 782.0 | DISTURBANCE OF SKIN SENSATION |
| ⊘ | 846.0 | SPRAIN AND STRAIN OF LUMBOSACRAL |
| ⊘ | 847.0 | NECK SPRAIN AND STRAIN |
| ⊘ | 847.1 | THORACIC SPRAIN AND STRAIN |
| ⊘ | 847.2 | LUMBAR SPRAIN AND STRAIN |
| ⊘ | 848.3 | SPRAIN AND STRAIN OF RIBS |
| ⊘ | 922.1 | CONTUSION OF CHEST WALL |
| ⊘ | 922.31 | CONTUSION OF BACK |
| ⊘ | 924.21 | CONTUSION OF ANKLE |
| ⊘ | 953.2 | INJURY TO LUMBAR NERVE ROOT |
| ⊘ | 959.9 | INJURY OTHER AND UNSPECIFIED UNSPECIFIED SIDE |

847 Sprains and strains of other and unspecified parts of back
847.2 Lumbar sprains and strains Return-To-Work Summary Guidelines

| Dataset | Midrange | At-Risk |
|---|---|---|
| Claims data | 17 days | 59 days |
| All absences | 10 days | 37 days |

Return-To-Work "Best Practice" Guidelines
Mild (grade I), clerical/modified work: 0 days
Mild, manual/heavy manual work: 7-10 days
Severe (grade II-III), clerical/modified work: 0-3 days
Severe, manual work: 14-17 days
Severe, heavy manual work: 35 days
With radicular signs, see 722.1 (disc disorders)
Obesity comorbidity (BMI>=30), multiply by: 1.31

Capabilities & Activity Modifications for Restricted Work:
Clerical/modified work: Lifting with knees (with a straight back, no stooping) not more than 5 lbs up to 3 times/hr; squatting up to 4 times/hr; standing or walking with a 5-minute break at least every 20 minutes; sitting with a 5-minute break every 30 minutes; no extremes of extension of flexion; no extremes of twisting; no climbing ladders; driving car only up to 2 hrs/day.
Manual work: Lifting with knees (with a straight back) not more than 25 lbs up to 15 time/hr; squatting up to 16 times/hr; standing or walking with a 10-minute break at least

FIG. 17

| Reference Points | Financial Reference (28) | Medical Reference (28) | Disability Reference | Diagnoses | DxCAT Analysis |
|---|---|---|---|---|---|

⎡ 727

Primary DxCAT Timeline

| Days | DxCAT | DiagCode | DiagDescr |
|---|---|---|---|
| 30 | 105031001 | 826.0 | FX PHALANX/FOOT-CLOSED |
| 60 | 105031001 | 826.0 | FX PHALANX/FOOT-CLOSED |
| 90 | 105031001 | 826.0 | FX PHALANX/FOOT-CLOSED |
| Current | 105031001 | 826.0 | FX PHALANX/FOOT-CLOSED |

Primary DxCAT Analysis

| At day 105 | At Closure | Claim Count | % | DxGroup | DxSubGroup | DxBodySystem | DxLocation | DxDetail |
|---|---|---|---|---|---|---|---|---|
| 105031001 | 105031001 | 28 | 93.33 | Trauma | Fracture, single or multiple, without other injury type specified | Musculo-skeletal system, soft tissue and connective tissue | Fingers or toes | Localized, closed; only minor complication if any |
| | 100091008 | 1 | 3.33 | Trauma | Misc. or type not specified | Skin, subcutaneous tissue & mucous membranes | Fingers or toes | Severe, open, prolonged, uncontrolled, progressive, multiple sites or disseminated |
| | 105031008 | 1 | 3.33 | Trauma | Fracture, single or multiple, without other injury type specified | Musculo-skeletal system, soft tissue and connective tissue | Fingers or toes | Severe, open, prolonged, uncontrolled, progressive, multiple sites or disseminated |

DETERMINING LIKELY OUTCOMES OF ACTIVE INSURANCE CLAIMS BY CALCULATING AND EXAMINING AGGREGATED OUTCOMES OF MATCHING HISTORIC CLAIMS

TECHNICAL FIELD

This disclosure relates to the processing of insurance claims, including workers' compensation claims, healthcare claims, and automobile accident claims.

DESCRIPTION OF RELATED ART

Insurance claims, including workers' compensation claims and automobile accidents claims, are routinely processed by insurance companies and others on their behalf. Reserves must usually be set aside for the payment of these claims and amounts are sometimes paid in settlement of them. The reserves are set aside and the settlements are sometimes made before all information about the claims is known, such as before all medical treatments have been provided or even prescribed.

Claim handlers and others are therefore often forced to estimate the ultimate costs of these claims. These estimates, however, can be significantly inaccurate. This can result in far too much or far too little being set aside in reserves and/or far too much being paid in settlements. The sheer volume of information that these people must manage can also sometimes cause them not to act promptly in connection with claim events, leading to an even worse claim outcome.

SUMMARY

An insurance claim analysis system may generate information indicative of an outcome of an active insurance claim. A historic insurance claim information database may hold historic information about historic insurance claims. A database query module may query the historic insurance claim information database for historic insurance claims that match search criteria indicative of one or more aspects of the active insurance claim. A data aggregation module may calculate an aggregate of an aspect of the historic information about the historic insurance claims that match the search criteria or a subset thereof. A report generation module may generate a report that includes the calculated aggregate of the aspect of the historic information.

The historic insurance claims may include closed insurance claims.

An active insurance claim information database may hold information about active insurance claims. A query formulation module may automatically formulate the search criteria based on information about an identified active insurance claim in the active insurance claim information.

A user interface may allow a user to modify at least a portion of the search criteria automatically formulated by the query formulation module.

The user interface may allow a user to identify a subset of the historic insurance claims that match the search criteria. The search criteria may include criteria limiting the search to the identified subset of the historic insurance claims.

The historic insurance claims and the active insurance claim may both be for compensation for personal injury.

The historic insurance claim information for each historic insurance claim may include a primary diagnosis category indicative of a related group of diagnoses, one of which has been identified as being primarily responsible for the outcome of the historic insurance claim. The search criteria may include a primary diagnosis category indicative of a related group of diagnoses, one of which has been identified as being primarily responsible for the outcome of the active insurance claim.

There may be different ways of determining which diagnosis is primarily responsible for the claim outcome. The user interface may allow a user to select one of these different ways. The primary diagnosis category included with the search criteria may be the one that includes the diagnosis determined to be primarily responsible for the outcome of the active insurance claim based on the way selected through the user interface.

The historic information about some of the historic insurance claims may include one or more co-morbidity factors. Each may be indicative of a complicating medical factor relating to the historic insurance claim. The search criteria may include at least one co-morbidity factor indicative of a complicating medical factor relating to the active insurance claim.

At least one co-morbidity factor may be an inflammatory condition or a degenerative condition. The search criteria formulated by the query formulation module may include one of these co-morbidity factors.

The historic information about each historic insurance claim may include an amount of money paid for an aspect of the historic insurance claim. The calculated aggregate of an aspect of the historic information may be an average of the amount of money paid on the aspect of the historic insurance claims that match the search criteria or a subset thereof.

The data aggregation module may be configured to break down the historic insurance claims that match the search criteria into sub-sets based on the amount of money that was paid on an aspect of the historic insurance claims. The calculated aggregate of the aspect of the historic information may be an average of the amount of money paid on the aspect of the historic insurance claims for each of the sub-sets.

The historic information about each historic insurance claim may include information indicative of each medical service that was provided in connection with the historic insurance claim and the type of that medical service. The calculated aggregate of an aspect of the historic information may be an average of the number of times a medical service of each type was sought in connection with the historic insurance claims that match the search criteria.

The historic information about each historic insurance claim may include information indicative of the payment made for each medical service that was provided in connection with the historic insurance claim and the type of that medical service. The calculated aggregate of an aspect of the historic information may be an average of the total payments made for a medical service of each type in connection with the historic insurance claims that match the search criteria.

The historic information about each historic insurance claim may include a number of disability days. The calculated aggregate of an aspect of the historic information may be an average of the number of disability days for the historic insurance claims that match the search criteria.

The historic information about some of the historic insurance claims may include one or more co-morbidity factors, each indicative of a complicating medical factor relating to the historic insurance claim. The calculated aggregate of an aspect of the historic information may include an average of the number of disability days for the historic insurance claims that match search criteria that includes at least one co-morbidity factor indicative of a complicating medical factor relating to the active insurance claim. The calculated aggregate of an aspect of the historic information may also include an average of the number of disability days for the historic insurance claims that match search criteria that does not include any co-morbidity factor indicative of a complicating medical factor relating to the active insurance claim.

The historic information about some of the historic insurance claims may each include information indicative of a change during the course of the historic insurance claim in a primary diagnosis category that has been identified as being primarily responsible for the historic insurance claim outcome. The calculated aggregate of an aspect of the historic information may be an aggregate of the number of the historic insurance claims that match the search criteria and that have an outcome indicative of no change during the course of the historic insurance claim in the primary diagnosis category.

The data aggregation module may be configured to calculate aggregates of multiple aspects, each of a different aspect of the historic information about the historic insurance claims that match the search criteria or a subset thereof.

Non-transitory, tangible, computer-readable media may contain a program of computer instructions configured to implement one or more of the processes described herein for generating information indicative of an outcome of an active insurance claim when run in a computer system.

These, as well as other components, steps, features, objects, benefits, and advantages, will now become clear from a review of the following detailed description of illustrative embodiments, the accompanying drawings, and the claims.

BRIEF DESCRIPTION OF DRAWINGS

The drawings are of illustrative embodiments. They do not illustrate all embodiments. Other embodiments may be used in addition or instead. Details that may be apparent or unnecessary may be omitted to save space or for more effective illustration. Some embodiments may be practiced with additional components or steps and/or without all of the components or steps that are illustrated. When the same numeral appears in different drawings, it refers to the same or like components or steps.

FIG. 6 illustrates a screen displaying an example of diagnostic fields of information in an active insurance claim.

FIG. 11 illustrates a portion of a screen that may appear when the "Medical Reference" tab 721 illustrated in FIG. 7 is selected, displaying an example of a bar graph report generated by the report generation module illustrated in FIG. 1 of aggregated medical treatment visit information provided by the data aggregation module illustrated in FIG. 1.

FIG. 12 illustrates a screen of the same information that is illustrated in FIG. 11 that may also or instead appear when the "Medical Reference" tab 721 is selected, except in a table format.

FIG. 14 illustrates a screen of the same information that is illustrated in FIG. 13 that may also or instead appear when the "Medical Reference" tab 721 is selected, except in a table format.

FIG. 16 illustrates a screen that may appear when the "Diagnoses" tab 725 illustrated in FIG. 7 is selected, displaying an example of a report generated by the report generation module illustrated in FIG. 1 of diagnosis information provided by the data aggregation module illustrated in FIG. 1

FIG. 17 illustrates a screen that may appear when the "DxCAT Reference" tab 727 illustrated in FIG. 7 is selected, displaying an example of a report generated by the report generation module illustrated in FIG. 1 of aggregated diagnostic information provided by the data aggregation module illustrated in FIG. 1.

DETAILED DESCRIPTION OF ILLUSTRATIVE EMBODIMENTS

Illustrative embodiments are now described. Other embodiments may be used in addition or instead. Details that may be apparent or unnecessary may be omitted to save space or for a more effective presentation. Some embodiments may be practiced with additional components or steps and/or without all of the components or steps that are described.

Figure 1:
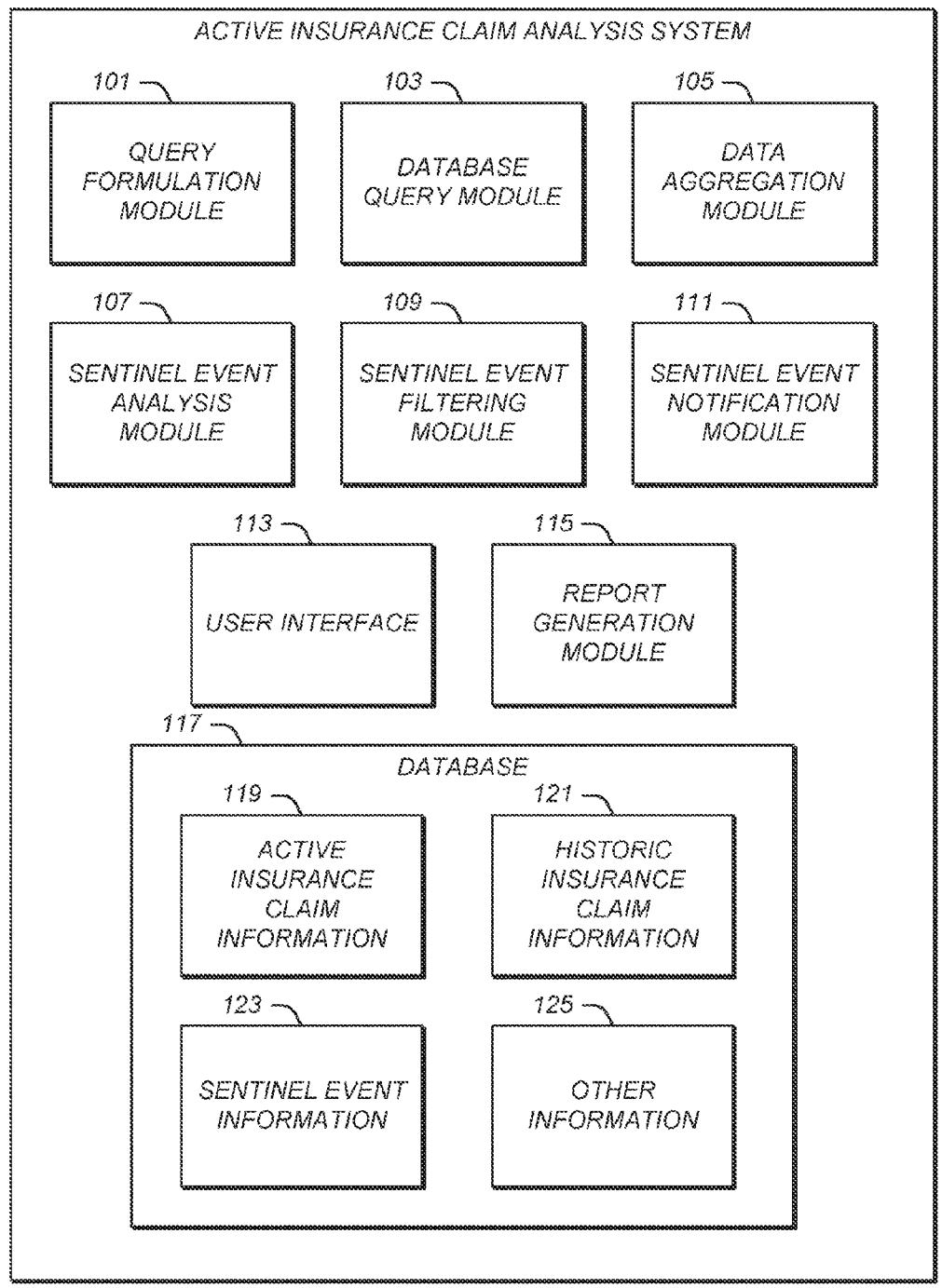
FIG. 1 illustrates an example of an active insurance claim analysis system.

FIG. 1 illustrates an example of an active insurance claim analysis system. As illustrated in FIG. 1, the active insurance claim analysis system may include a query formulation module 101, a database query module 103, a data aggregation module 105, a sentinel event analysis module 107, a sentinel event filtering module 109, a sentinel event notification module 111, a user interface 113, a report generation module 115, and a database 117. The database 117 may include active insurance claim information 119, historic insurance claim information 121, sentinel event information 123, and other information 125.

The database 117 may be a single database or multiple databases managed by a single or multiple database management system(s). The database 117 may all be at the same location or distributed across multiple locations.

The active insurance claim information 119 may be information about active insurance claims, that is, insurance claims whose files have not yet been closed. Closure of an insurance file may typically take place when all aspects of the insurance claim have been settled or otherwise resolved.

The historic insurance claim information 121 may be information about historic insurance claims. These may include or consist entirely of insurance claims that have progressed substantially toward closure and/or that have already been closed.

The insurance claims that are the subject of the active and historic insurance claim information may of type. For example, the insurance claims may be claims for personal injury, such as workers' compensation claims or automobile accident claims.

Figures 2, 3, 4, 5:
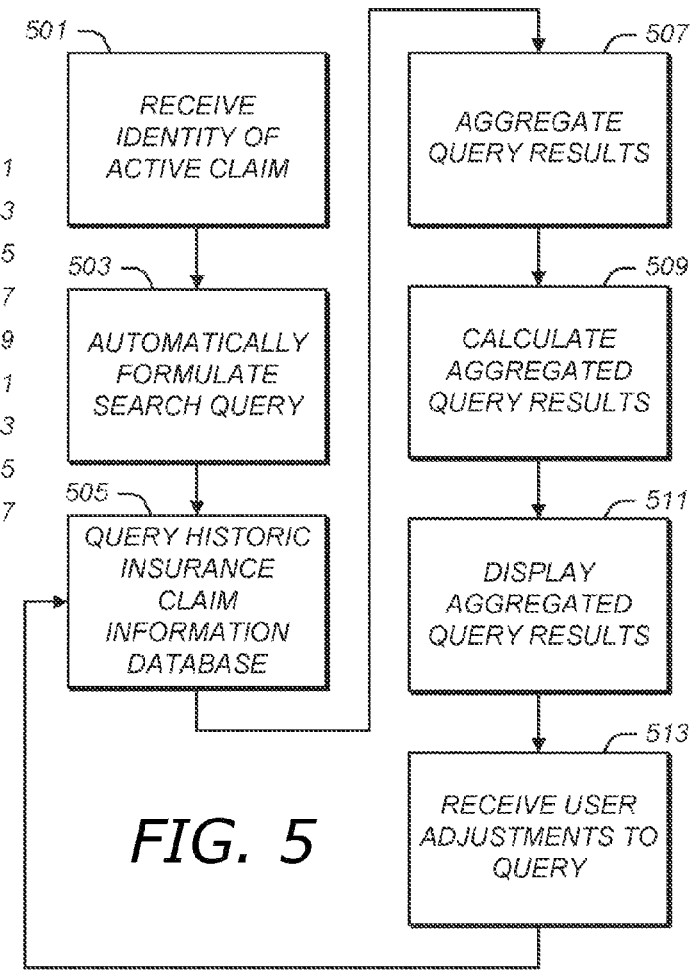
FIG. 2 illustrates an example of general information fields that may be present in connection with each claim in the historical and active insurance claim information database illustrated in FIG. 1.
FIG. 3 illustrates an example of diagnoses fields that may be present in connection with each claim in the historical and active insurance claim information database illustrated in FIG. 1.
FIG. 4 illustrates an example of co-morbidity fields that may be present in connection with each claim in the historical and active insurance claim information database illustrated in FIG. 1.
FIG. 5 illustrates an example of a process of analyzing an active insurance claim by calculating and examining aggregated outcomes of matching historic insurance claims or subsets thereof.

The information about each active and historic insurance claim may include various segregated and separately-accessible fields of information. Examples of these are illustrated in FIGS. 2-4. The database 117 may be created in whole or in part from exports from other database. Mappings may be used to automatically segregate information from the other databases into the database schema of the database 117 or such information may in whole or in part be segregated manually.

FIG. 2 illustrates an example of general information fields that may be present in connection with each claim in the historical and active insurance claim information illustrated in FIG. 1. As illustrated in FIG. 2, the information about each active and historic insurance claim may include an insurance claim number field 201, a claimant name field 203, a claimant age field 205, a claimant location field 207, a claimant sex field 209, a surgery field 211 indicating whether the claimant has had surgery relating to the claim, a litigation field 213 indicating whether litigation has been initiated relating to the claim, and a permanent disability field 215 indicating whether the claim has resulted in permanent disability. The information in the surgery field 211 may instead be generated in real-time, as needed, based on an analysis of CPT codes contained in medical bills that may also be part of the insurance claim information. Similarly, the information in the permanent disability field 215 may be generated in real-time, as needed, based on the presence of permanent disability benefits that may also be part of the insurance claim information.

There may be additional or different types of information fields associated with each insurance claim. Examples of these are discussed below in connection with other figures.

The information about each active and historic insurance claim may include one or more diagnoses relating to that claim.

FIG. 3 illustrates an example of diagnoses fields that may be present in connection with each claim in the historical and active insurance claim information database illustrated in FIG. 1.

As illustrated in FIG. 3, the information about each diagnosis may include a DiagDescr field 307. This field may include a description of the diagnosis.

Each diagnosis may include a DiagCode field 305. This field may include or consist of an ICD (International Classification of Diseases) that is indicative of the diagnosis.

Each diagnosis may include a DiagRank field 303. This field may rank the diagnosis as to whether it is perceived to be primarily influencing the outcome of the insurance claim, secondarily influencing the insurance claim outcome, or responsible in a tertiary way.

There may be different ways of determining which diagnosis is primarily influencing the outcome of the insurance claim, Each way may yield a different primary diagnosis. The way that is utilized may depend on the type of claim and/or the status of the information that has been received about the claim.

Workers' compensation claims, for example, may utilize a mythology for determining the primary diagnosis by giving preference to diagnoses that are indicative of trauma. Other types of claims may relate to general group health and may be based on medical data and the analysis of all diagnosis codes, without giving any preference to a specific code or group of codes.

The ranking of each diagnosis may be done manually or on an automated basis. The computer program known as Dyani Grouper published by Axiomedics Research may be used to do so automatically.

Some claims may not yet have any medical diagnosis. Such a diagnosis may nevertheless be supplied at least initially by the computer system based on the body part that has been injured and the nature of the injury. This information may be collected during claim intake and thus may always be available. In such a case when there are no medical diagnoses, a map may be prepared and utilized that maps each possible combination of body parts and natures of injury to the diagnosis code that most closely matches this information.

Each diagnosis may include a DXGroup field 309. This field may describe a group of diagnoses that are related clinically, financially, or otherwise. Each group may include the particular diagnosis that is indicated by the DiagDescr field 307 or the DiagCode field 305.

The determination of the value of the DxGroup field 309 for each diagnosis may be done manually or on an automated basis. The computer program known as Dyani Grouper published by Axiomedics Research may be used to do so automatically.

Each diagnosis may include a DXSubGroup field 311. This may be descriptive of a subgroup within the DxGroup field 309 in which the diagnosis falls.

Each diagnosis may include a DxBodySystem field 313. This may be indicative of a system or systems within the body that have been affected by the insurance claim.

Each diagnosis may include a DxLocation field 315. This may be indicative of the location or locations on or within the body that have been effected by the insurance claim.

Each diagnosis may include a DxDetail field 317. This may provide information that may be important, but that may not otherwise be apparent from the information in the other fields.

Each diagnosis may include a Diagnosis Category (Dx-CAT) field 301. The DxCAT field 301 may contain a single consolidated code indicative of the DxGroup 309, the DxSub-Group 311, the DxBodySystem 313, the DxLocation 315, and the DxDetail 317.

Each diagnosis may include additional or different fields of information.

The information about each active and historic insurance claim may include information about one or more co-morbidities, each of which may be indicative of a complicating medical condition relating to the insurance claim.

FIG. 4 illustrates an example of co-morbidity fields that may be present in connection with each claim in the historical and active insurance claim information database illustrated in FIG. 1. As illustrated in FIG. 4, the information about each insurance claim may include a field indicating which of several specified co-morbidities may be present, such as a mental disorders field 401, a diabetes field 403, a tobacco use field 405, an obesity field 407, a hypertension field 409, an inflammatory condition field 411, and a degenerative condition field 413. There may be additional or different co-morbidity fields.

Referring back to FIG. 1, the database query module 103 may be configured to query the historic insurance claim information 121 for historic insurance claims that match search criteria indicative of one or more aspects of an active insurance claim. These aspects may include or consist of the values within one or more of the fields of information that are contained within the active insurance claim information 119 in connection with a specific active insurance claim. The database query module 103 may be configured to limit matches to those historic insurance claims that contain fields of information that match all of the aspects specified in the search criteria or any logical combination of them. Fuzzy logic may or may not be employed in the matching.

FIG. 5 illustrates an example of a process of analyzing an active insurance claim by calculating and examining aggregated outcomes of matching historic insurance claims or subsets thereof. The query formulation module 101 may be configured to receive an identification of an active insurance claim, as reflected by a Receive Identity of Active Claim step 501.

FIG. 6 illustrates a screen displaying an example of diagnostic fields of information in an active insurance claim. A user may enter an active insurance claim number 601 and click a generate report button 603. The database query module 103 may query the active insurance claim information 117 for information about this identified active insurance claim and all or portions of this information may be displayed, such as is shown in FIG. 6.

The query formulation module 101 may be configured to automatically formulate the search criteria based on the identified active insurance claim, as reflected by an Automatically Formulate Search Query step 503. During this step, the query formulation module 101 may review the insurance claim information 119 about the identified active insurance claim and automatically formulate the search criteria based on this reviewed information.

For example, the query formulation module 101 may use as part of the search query the value of the DxGroup field 309 for the latest diagnosis that is indicated as being the primary cause of the outcome of the insurance claim in the DiagRank field 303 of this record. This may insure a larger group of relevant hits than if the DiagCode field 305 or the DiagDescr field 307 were used instead.

The query formulation module 101 may instead use the value of a more restrictive field such as the DxCAT field 301 of the latest diagnosis that is indicated as being the primary cause of the outcome of the insurance claim (referred to hereinafter as the "primary DxCAT value"). This may still insure a larger group of relevant hits than if the DiagCode field 305 or the DiagDescr field 307 was used, but more restrictive than if the DxGroup field 309 was used.

Figure 7:
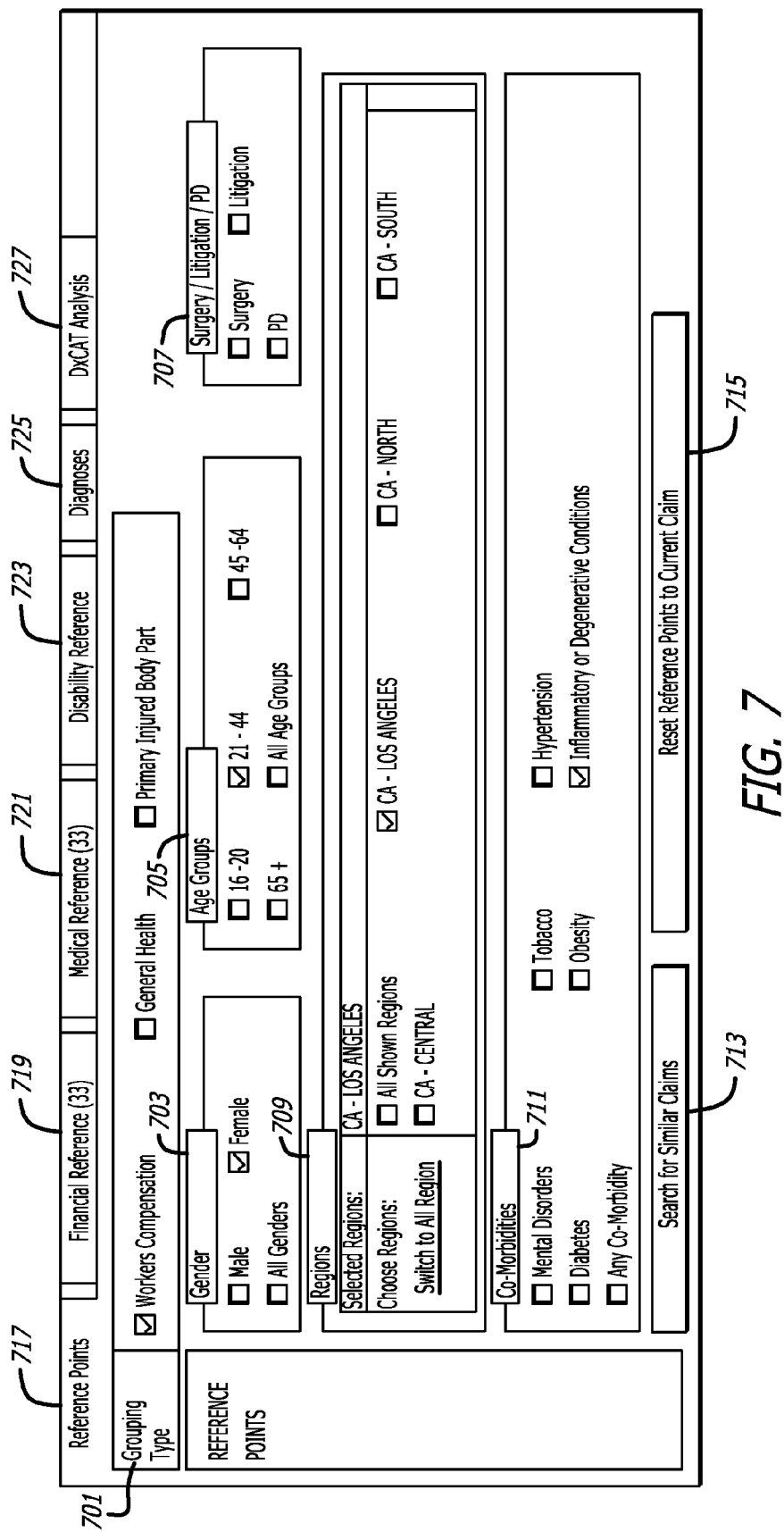
FIG. 7 illustrates a screen that may appear when the "Reference Points" tab 717 illustrated in FIG. 7 is selected, displaying an example of a query automatically formulated by the query formulation module illustrated in FIG. 1.

FIG. 7 illustrates a screen that may appear when the "Reference Points" tab 717 illustrated in FIG. 7 is selected, displaying an example of a query automatically formulated by the query formulation module illustrated in FIG. 1. The screen in FIG. 7, as well as the screens illustrated in FIGS. 8, 11-15, and 17 that are discussed below, may appear with the screen illustrated in FIG. 6, such as below it. One or more of these screens may instead be separate from the screen illustrated in FIG. 6.

As illustrated in FIG. 7, the query formulation module 101 has automatically formulated the search query based on various information about the identified active insurance claim in the active insurance claim information 119 and presented this information as a default search query in a graphic, interactive user interface.

For example, the query formulation module 101 may indicate the way in which the diagnosis that was primarily responsible for the outcome of the active insurance claim was determined in a "Grouping Type" section 701. In the example illustrated, it indicates that the "Worker's Compensation" algorithm was used in determining this primary diagnosis. In other cases, a "General Health" approach might be used which, as explained, above, may not give any preference to any type of diagnosis. In still other cases, a "Primary Injured Body Part" approach might have been used which, as explained above, may be based on the body part that was reported to be injured and the nature of the injury.

The query formulation module 101 may display the sex of the claimant from the sex field 209 in a "Gender" section 703; the age of the claimant from the age field 205 in an "Age Group" section 705, whether there has been surgery, litigation, or a permanent disability, as indicated in the surgery field 211, the litigation field 213, and the permanent disability field 215, respectively, in a "Surgery/Litigation/PD" section 707; the location of the claimant from the location field 207 in a "Regions" section 709, and the co-morbidities as indicated in the co-morbidities fields illustrated in FIG. 4 in a "Co-Morbidities" section 711. The information illustrated in FIG. 7 thus constitutes the search query that the query formulation module 101 has automatically extracted from the identified active insurance claim. One exception may be the value of the primary DxCAT value. This may instead be displayed on the screen illustrated in FIG. 6, which may in fact be part of the screen that is illustrated in FIG. 7.

The database query module 103 may be configured to automatically query the historic insurance claim information 121 for historic insurance claims that contain fields of information that match all of the fields of information in the search query, as indicated in FIG. 7, and as including the primary DxCAT value discussed above. This is reflected in FIG. 5 as a Query Historic Insurance Claim Information Database step 505.

The results of this query may be provided by the database query module 103 to the data aggregation module 105. The data aggregation module 105 may calculate an aggregate of one or more aspects of the historic information about the historic insurance claims that match the search criteria or a subset thereof, as reflected in an Aggregate Query Results step 507.

The report generation module 115 may generate various reports that include one or more of the calculated aggregates of the one or more of the aspects of the historic information and cause one or more of these reports to be selectively displayed using the user interface 1113, as reflected by a Display Aggregated Query Results step 509. Examples of these various reports and of the aggregated information which they contain is discussed below in connection with a discussion of FIGS. 8-15 and FIG. 17.

At any time before or after the user has viewed any of these reports, the user may decide to change the default search query for various reasons. For example, the number of matches that result from the default query may be too small to be statistically meaningful. Other reasons for changing the default query may include researching a possible change in claim outcome if it becomes litigated, if a surgery is performed, if the claimant moves to another region, and/or if one or many co-morbidities are discovered, To facilitate this change, the user interface 113 may include a mouse and/or keyboard that may enable the user to alter the default search criteria that is illustrated in FIG. 7 as checked items. For example, the user may check a different approach for diagnostic ranking in the "Grouping Type" section 701; a different gender or all genders in the "Gender" section 703; a different age group or all age groups in the "Age Groups" section 705; a different combination of the selections in the "Surgery/Litigation/PD" section 707; a different region or all regions in the "Regions" section 709; and/or a different set of or no co-morbidities in the "Co-Morbidities" section 711. This is reflected in a Receive User Adjustments to Query step 513 in FIG. 5. After making these query changes, the user may click a "Search For Similar Claims" button 713 in FIG. 7. This may cause the database query module 103 to re-query the historic insurance claim information 121 to obtain a new set of claims that match the revised search query.

The user may repeat this "What If" process as many times as desired. At any point during the process, the user may instead click a "Reset Reference Points To Current Claim" button 715 to reset the search query to the default search query originally formulated by the query formulation module 101, in which case the database query module 103 may again query the historic insurance claim information 121 using the default search criteria.

The historic insurance claim information 121 may include information about amounts of monies paid for one or more aspects of each historic insurance claim, such as money paid for medical expenses ("Medical"), indemnity for pain, suffering, and other losses ("Indemnity"), attorneys' fees and other claim expenses ("Allocated"), settlement ("Fin Settl Pmt"), and permanent disability ("PD Paid"). The historic insurance claim information 121 may also include information about the total number of days and weeks of disability ("TD Days/Wks") and the total number of days and weeks that the claim was open ("Open Days/Wks").

Figure 8:
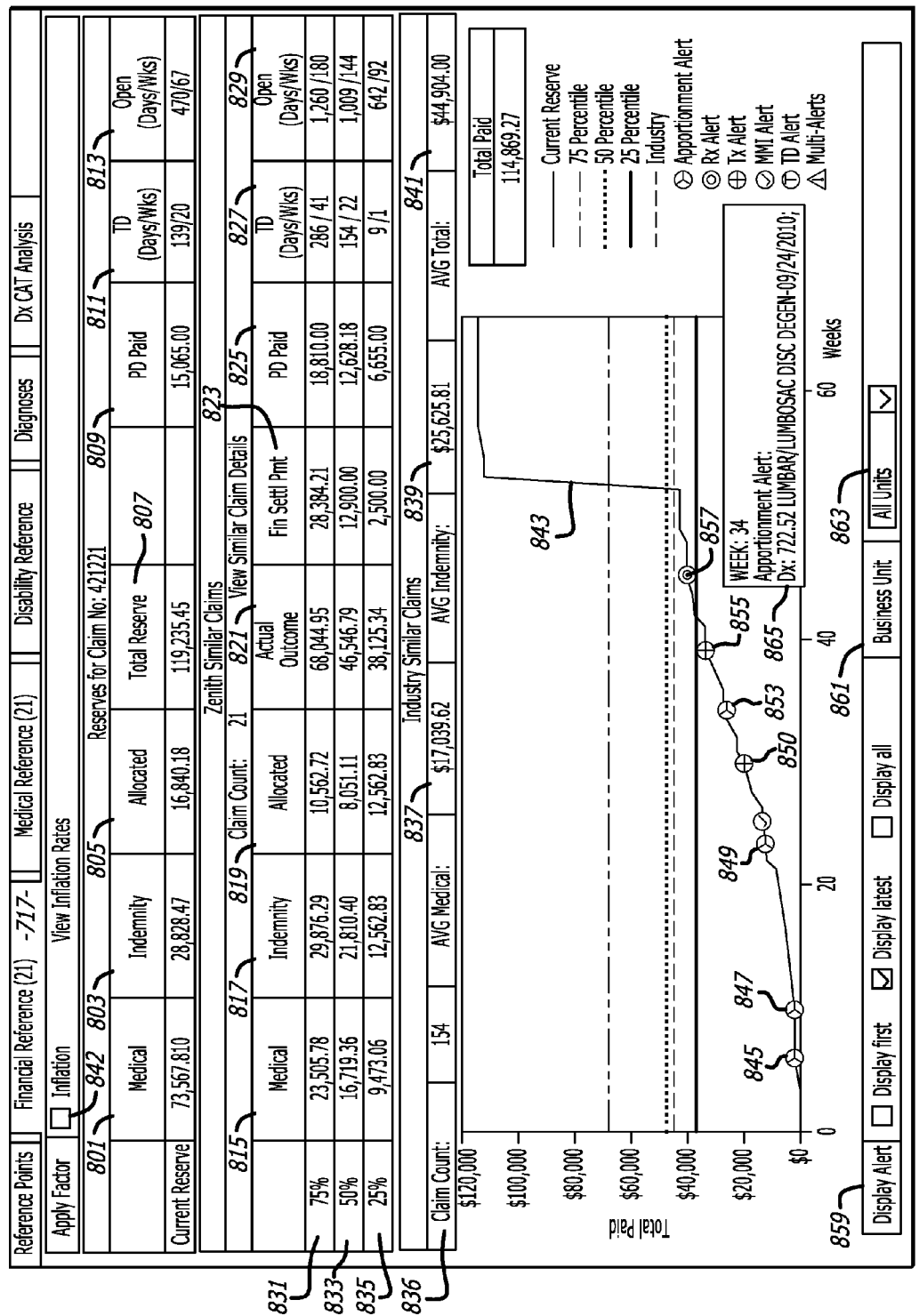
FIG. 8 illustrates a screen that may appear when a "Financial References" tab 719 illustrated in FIG. 7 is selected, displaying an example of a report generated by the report generation module illustrated in FIG. 1 of aggregated financial information provided by the data aggregation module illustrated in FIG. 1.

FIG. 8 illustrates a screen that may appear when the "Financial Reference" tab 719 illustrated in FIG. 7 is selected, displaying an example of a report generated by the report generation module illustrated in FIG. 1 of aggregated financial information provided by the data aggregation module illustrated in FIG. 1.

As illustrated in FIG. 8, the report provided by the report generation module 115 when the "Financial Reference" tab 719 is selected may include information about reserves that have been set aside for the identified active insurance claim, such as reserve information about "Medical" 801, "Indemnity" 803, "Allocated" 805, and a "Total Reserve" 807 of all of the reserves. The screen may also display "PD Paid" 809 providing information about the total amount already paid for permanent disability, "TD Days/Wks" 811 providing information about the number of days and weeks of temporary disability that have thus-far accumulated, and "Open Days/Wks" 813 providing information about the number of days and weeks the claim has been open.

This information may be contrasted by the user with ranked numbers that the data aggregation module 105 has compiled relating to the historic insurance claims that match the search criteria or a portion thereof, such as the payments for "Medical" 815, "Indemnity" 817, "Allocated" 819, "Actual Outcome" 821 (the total of Medical, Indemnity, and Allocated), "Fin Settl Pmt" 823, "PD Paid" 825, "TD Days/Wks" 827, and "Open Days/Wks" 829 (indicating the total number of days and weeks the matching historic claims were open). These contrasts may enable the user to determine the likely outcomes of the identified active insurance claim in these areas. For example, and as shown in FIG. 8, information in the "Total Reserves" 807 may represent an anticipated total of the outcome for a claim, which may be considered at the time of reserving. Information in the "Actual Outcome" 821 may represent the outcome of similar claims as defined by the search query in FIG. 7, aggregated by the data aggregation module 105 into 75% group 831, 50% group 833, and 25% group 835. For example, the anticipated outcome as set forth in the "Total Reserve" 807 significantly exceeds 75% of the historic "Actual Outcome" 821, thus possibly justifying a reduction in the reserve for this active claim.

As indicated, the data aggregation module 105 may rank historic outcomes in subgroups, as illustrated by a "75%" row 831, a "50%" row 833, and a "25%" row 835. Each number in each row may be the value of the percentage of claims defined by the row that closed at or below the number that is listed. For example, the number "116,719.36" in the "Medical" 815 column of the "50%" row 833 means that the medical payments for 50% of the matching claims were at or below this number. Each of these rows may be in a different color to aid in their differentiation.

Averages for similar historic claims obtained from other data sources, such as from other insurance carriers, may separately be listed, as reflected by a "Claim Count" 836, an "AVG Medical" 837, an "AVG Indemnity" 839, and an "AVG Total" 841 for "Industry Similar Claims."

An "Inflation" check box 842 may be provided. When checked by a user, the data aggregation module 105 may be configured to cause the outcome of each historic claim included in the aggregation to be adjusted for inflation based on the date of injury and relevant inflation data.

A graph 843 may be provided showing the payments that have thus-far accumulated for the identified active insurance claim during its pendency. The occurrence of sentinel events that are likely to have a significant effect on the outcome of the identified active insurance claim may also be shown on this graph, such as sentinel events 845, 847, 849, 851, 853, 855, and 857 as illustrated in FIG. 8.

These sentinel events may be of various types.

One type of sentinel event may be a prescription for a pharmaceutical that is likely to have a significant effect on the outcome of the insurance claim, such as a prescription for opiates, anti-depressants, or impotence agents. These events are indicated in FIG. 8 as an "RX Alert."

Another type of sentinel event may be a request for treatment that is likely to have a significant effect on the outcome of the insurance claim, such as a request for treatment that includes surgery, an injection, or a consultation with a specialist. These events are indicated in FIG. 8 as a "Tx Alert."

Another type of sentinel event may be a determination that the patient is not likely to benefit from further treatment. These are indicated in FIG. 8 as an "MMI (Maximum Medical Improvement) Alert."

Another type of sentinel event may be a diagnosis of a degenerative condition that may then call for a disability apportionment. These are indicated in FIG. 8 as an "Apportionment Alert."

Another type of sentinel event may be an indicator of temporary disability duration exceeding Official Disability Guidelines. These are indicated in FIG. 8 as a "TD Alert."

When multiple alerts fall within the same time period, they may be visually aggregated into a single icon. Each of these are indicated in FIG. 8 as a "Multi-Alert."

There may be other types of sentinel events in addition or instead. These may include, for example social events (such as divorce and child birth), employment-related events (such as availability of modified duties to accommodate for temporary disability and loss of employment) and/or legal events (such as attorney representation, a request for treating doctor's deposition, and a trial decision).

The sentinel event analysis module 107 may determine the presence of these sentinel events by reviewing the active insurance claim information 119 for the identified active insurance claim. The report generation module 115 may generate a report of the sentinel events identified by the sentinel event analysis module 107, such as the icons illustrated in the bottom portion of FIG. 8 and discussed above.

The sentinel event information 123 that is contained within the database 117 may contain a list of each event during the course of an active insurance claim that is considered to be a sentinel event, i.e., each event that is likely to have a significant effect on the outcome of an active insurance claim. As part of the process of identifying these sentinel events, the sentinel event analysis module 107 may cause the database query module to query the active insurance claim information 119 in connection with the identified active insurance claim for the purpose of identifying each event within this information that matches one of the sentinel events listed in the sentinel event information 123. A change in the sentinel event information 123 can thus be made to effectuate a change in the sentinel events that are identified by the sentinel event analysis module 107 and reported by the report generation module 115.

Hovering a mouse over a sentinel alert may cause details of that alert to be displayed, such as alert details 865 for the alert 853.

The sentinel event filtering module 109 may be configured to filter the sentinel events that are displayed by filtered criteria. In a display alert section 859 of the screen which is illustrated in FIG. 8, for example, a user may select whether to display only the first sentinel event ("Display first") of each type, only the last event ("Display last") of each type, or all sentinel events ("Display all"). Alerts of the same type but with different underlying details may be considered different alerts by these filter criteria.

The sentinel event filtering module 109 may also or instead be configured to filter the sentinel events that are displayed based on a business unit to which they relate, as selected by a user in a in a drop down box 863 in a "Business Unit" section 861. Possible options that the user may select as filtering criteria in this section may include a "Claims Function," a "Medical Management Function," a "Legal Function," or "All [Business] Units."

Each of these types of business units may be mapped to different types of sentinel events. For example, the "Claims Function" may be mapped to the sentinel events that are based on requests for treatment, prescriptions for pharmaceuticals, determinations that the patient is not likely to benefit from further treatment, and diagnosis of degenerative conditions. Similarly, the "Medical Management Function" may be mapped to sentinel events based on request for treatments, prescriptions for pharmaceuticals, or determinations that the patient is not likely to benefit from further treatment. Similarly, the "Legal Function" may be mapped to sentinel events based on determinations that the patient is not likely to benefit from further treatment or diagnosis of degenerative conditions.

Different types of filtering criteria may in addition or instead be provided in connection with the "Display Alert" section 859 and/or the "Business Unit" section 861.

Figure 9:
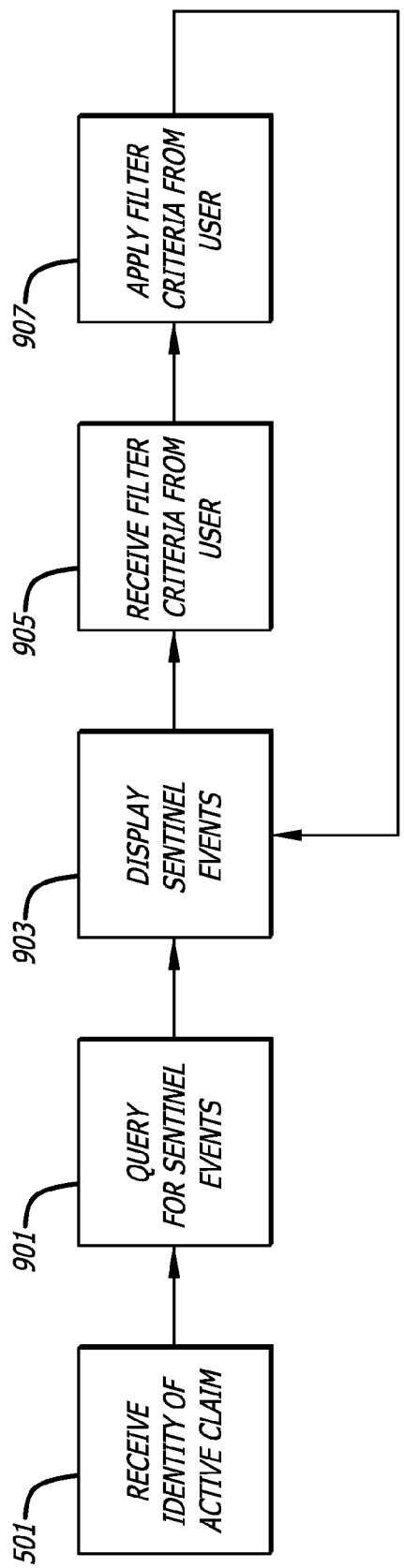
FIG. 9 illustrates an example of a process of analyzing an active insurance claim by examining sentinel claim events.

FIG. 9 illustrates an example of a process of analyzing an active insurance claim by examining sentinel claim events. The query formulation module 101 may receive an identification of an active insurance claim, as reflected by a Receive Identity of Active Claim step 501. This may be the same step 501 that is illustrated in FIG. 5 and discussed above. The sentinel event analysis module 107 may then cause the database query module 103 to query the active insurance claim information 119 for sentinel events in connection with the identified active insurance claim, as reflected by a Query For Sentinel Events step 901. The sentinel events identified in the sentinel events information 123 may be used in the query. The report generation module 115 may then generate a report of these sentinel events and cause them to be displayed on a display in the user interface 113, as illustrated by a Display Sentinel Events step 903. Filter criteria may then be applied by the user, as illustrated and discussed above in connection with the "Display Alert" section 859 and the "Business Unit" section 861, as reflected by a Receive Filter Criteria from User step 905. These filter criteria may be applied by the sentinel event filtering module 109, as reflected by an Apply Filter Criteria from User step 907. The filtered results may then be displayed, following which adjustments to the filtering criteria may be made.

The sentinel event notification module 111 may monitor the active insurance claim information 119 in the database 117 as it is entered or otherwise arrives. The sentinel event notification module 111 may analyze this information for the purpose of determining whether any of it indicates the occurrence of a sentinel event, as defined by the sentinel event information 123. Upon the detection of each new sentinel event, the sentinel event notification module 111 may issue an alert to one or more persons or other systems of the existence of the sentinel event. Each alert may include information identifying the active insurance claim in which the sentinel event was detected, as well as information identifying the sentinel event. This may assist such persons or systems, such as by giving them the opportunity to take proactive measures that may aid in the management of the active insurance claim that is associated with the sentinel event.

The sentinel events that are subject to the notifications issued by the sentinel event notification module 111 may be subject to user-specified filtering, thus reducing the number of notifications that are issued. The recipients of the notifications issued by the sentinel event notification module 111 may be dependent upon the nature of the sentinel event. For example, notifications of sentinel events that are of importance to one type of business unit may be sent to one person or system, while sentinel events that are relevant to another type of business unit may be sent to a different person or system.

The user may wish to exclude certain historic insurance claims from the calculation of aggregate information by the data aggregation module for various reasons, such as to remove historic claims that appear to be aberrations.

There are numerous other applications for sentinel events that the system pay be configured to provide. These include using the absence of these events to ascertain likely claim outcome, using regression analysis of claims data to calculate the likelihood of such events for various claims and/or their likely effect on claim outcome, using these likelihood calculations during the reserving process, re-evaluating reserves in view of historic, new and/or or predicted sentinel events, and establishing and mandating optimal procedures in response to each event.

These various uses of sentinel events may be combined and presented to create more proactive claims handling. For example, if a certain type of injury should not warrant prolonged use of opioids, a sentinel event may be triggered based upon the second dispensing of opioids that may lead to a nurse being staffed on the file, a change in provider, an increase reserve, or all three of these actions and potentially others.

Figure 10:
FIG. 10 illustrates a screen displaying an example of a report generated by the report generation module illustrated in FIG. 1 of individual historic insurance claims that were determined to match search criteria by the database query module illustrated in FIG. 1.

FIG. 10 illustrates a screen displaying an example of a report that may be generated by the report generation module 115 illustrated in FIG. 1 of individual historic insurance claims that were determined to match search criteria by the database query module 103 illustrated in FIG. 1. As illustrated in FIG. 10, the screen may include information about each matching historic insurance claim that may aid the user in determining which should be excluded from the calculation of aggregate information. The user may select those matching individual historic insurance claims that should be included in the aggregate calculation, following which the user may click an "Apply Selections" button 1001. In turn, this may cause new aggregate information to be calculated by the data aggregation module 105 based only on the matching historic insurance claims that the user selected on the screen illustrated in FIG. 10.

The historic insurance claim information 121 may include information indicative of each medical service that was provided in connection with the historic insurance claim and the type of that medical service. The calculated aggregate provided by the data aggregation module 105 may include an average of the number of times a medical service of each type was sought in connection with the historic insurance claims that match the search criteria.

FIG. 11 illustrates a portion of a screen that may appear when the "Medical Reference" tab 721 illustrated in FIG. 7 is selected, displaying an example of a bar graph report generated by the report generation module 115 illustrated in FIG. 1 of aggregated medical treatment visit information provided by the data aggregation module 105 illustrated in FIG. 1. FIG. 11 thus illustrates these averages for each type of medical service. The screen illustrated in FIG. 11 also illustrates national averages that may be obtained from other carriers or medical data aggregators, as well as the average and maximum numbers published in the "Official Disability Guideline." This data may also be stored in the database 117 as part of the other information 125, accessed by the database query module 103, and reported by the report generation module 115. Different colors may be used to signify the different sources of historic claim information.

FIG. 12 illustrates a screen of the same information that is illustrated in FIG. 11 that may also or instead appear when the "Medical Reference" tab illustrated in FIG. 7 is selected, except in a table format. Each entry of aggregate figures about the active insurance claim may be color coded to reflect its similarity to the corresponding average information about the matching historical insurance claims. For example, the aggregate information about a type of service for the active insurance information claim may be colored green to indicate that it is at or below 50% of the corresponding average for historic claims experience, yellow for between 50% and 75%, and red for those that exceed 75% of corresponding services utilization as experienced in historic claims.

Figure 13:
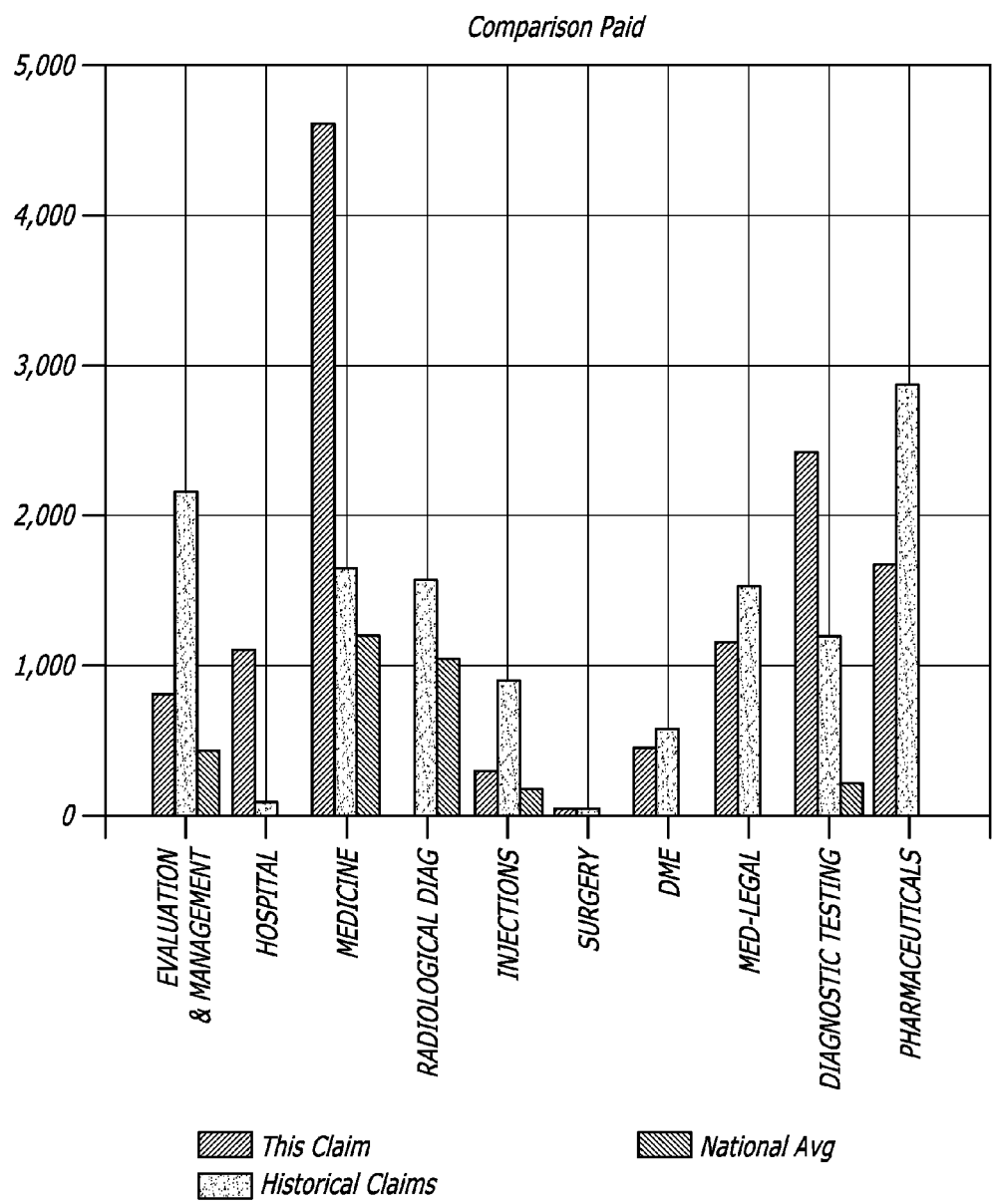
FIG. 13 illustrates a portion of a screen that may also or instead appear when the "Medical Reference" tab 721 illustrated in FIG. 7 is selected, displaying an example of a bar graph report generated by the report generation module illustrated in FIG. 1 of aggregated medical treatment cost information provided by the data aggregation module illustrated in FIG. 1.

FIG. 13 illustrates a portion of a screen that may also or instead appear when the "Medical Reference" tab 721 illustrated in FIG. 7 is selected, displaying an example of a bar graph report generated by the report generation module illustrated in FIG. 1 of aggregated medical treatment cost information provided by the data aggregation module 105 illustrated in FIG. 1. This is comparable to the screen illustrated in FIG. 11, except that the Y axis provides the average cost of each type of medical service for the matching historic insurance claims, rather than the number of times the service was provided. Again, different colors may be used to highlight the different information sources.

FIG. 14 illustrates a screen of the same information that is illustrated in FIG. 13 that may also or instead appear when the "Medical Reference" tab illustrated in FIG. 7 is selected, except in a table format. Again, colors may be used in the same way as discussed above in connection with FIG. 12.

The active insurance claim information 119 and historic insurance claim information 121 may include information about the number of disability days that have been suffered in connection with each claim.

Figure 15:
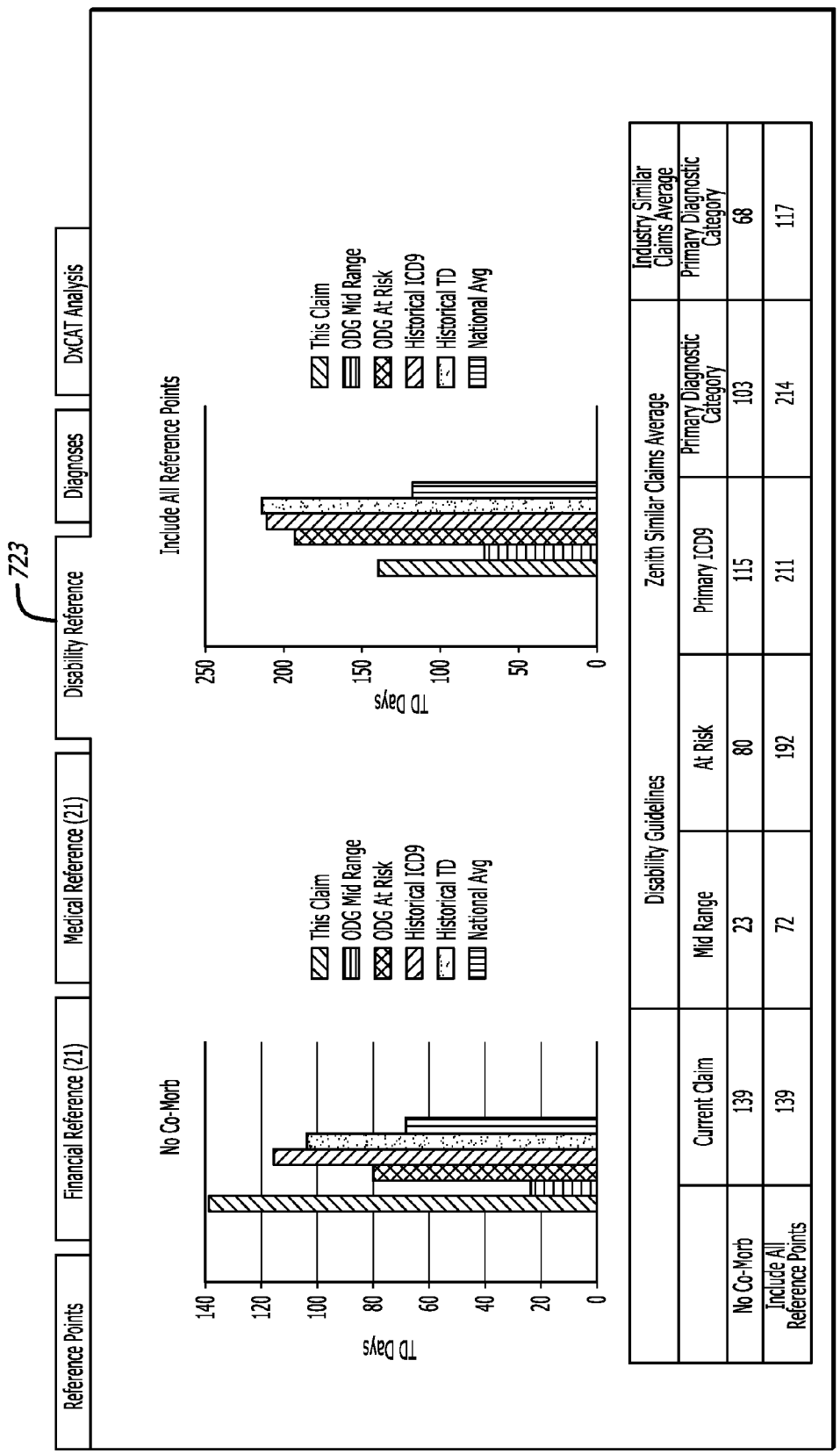
FIG. 15 illustrates a screen that may appear when the "Disability Reference" tab 723 illustrated in FIG. 7 is selected, displaying an example of a report generated by the report generation module illustrated in FIG. 1 of aggregated disability information provided by the data aggregation module illustrated in FIG. 1.

FIG. 15 illustrates a screen that may appear when the "Disability Reference" tab 723 illustrated in FIG. 7 is selected, displaying an example of a report generated by the report generation module 115 illustrated in FIG. 1 of aggregated disability information provided by the data aggregation module 105 illustrated in FIG. 1. As illustrated in FIG. 15, these number of days may be compared to the average number of days for the historic insurance claims that match the search criteria, as well as to a national average and the midrange and at risk numbers provided in the Official Disability Guide.

Normally, disability duration is calculated for a single diagnosis. Official Disability Guidelines represent a crosswalk between an individual diagnosis code (ICD code) and projected disability duration for a person diagnosed. In reality, injuries often result in conditions that cannot be described by a single diagnosis. To accommodate for this common situation, the duration of a disability may be calculated by two different methods The first method may add average disability duration for a diagnostic category (DxCAT) to which the primary diagnosis belongs. This can be achieved by averaging disability duration as defined by the guidelines for all diagnosis codes included into each diagnosis category. A second method may allow for identification of the primary diagnosis code and the most severe in terms of disability duration co-morbid condition and calculate an aggregate probable disability duration using the following commutation formula:

(Longest disability duration of primary or the most severe condition)+½(shortest of primary or the most severe condition)

where "the most severe condition" is defined as any diagnosis code that is associated with the longest disability duration as identified by Official Disability Guidelines.

The same information may be summarized in a table format, as also illustrated in FIG. 15.

FIG. 16 illustrates a screen that may appear when the "Diagnoses" tab 725 illustrated in FIG. 7 is selected, displaying an example of a report generated by the report generation module 115 illustrated in FIG. 1 of diagnosis information provided by the data aggregation module 105 illustrated in FIG. 1. This screen may include a table at the left that lists all of the diagnosis that have been provided in connection with the identified active insurance claim. A user may then select a particular diagnosis, following which a window on the right may open setting forth more information about that diagnosis, such as information about it that is obtained from the "Official Disability Guide," which may be part of the other information 125 in the database 117.

FIG. 17 illustrates a screen that may appear when the "DxCAT Reference" tab 727 illustrated in FIG. 7 is selected, displaying an example of a report generated by the report generation module 115 illustrated in FIG. 1 of aggregated diagnostic information provided by the data aggregation module 105 illustrated in FIG. 1. The top table in FIG. 17 may illustrate changes in the primary Diag Code 305 and primary DxCAT 301 as the identified active insurance claim has matured. The bottom table in FIG. 17 may reflect aggregate information calculated by the data aggregation module 105 of the same type in connection with the historic insurance claims that match the search criteria and that have the same primary DxCAT at the same point of maturity as the active insurance claim.

The primary diagnosis category from the DxCAT field 301 that may be used in the search criteria for this as well as the other screens may be the primary diagnosis category that was last identified in connection with the identified active insurance claim.

The primary diagnosis category from the DxCAT field 301 in the historic insurance claims that is matched to the primary diagnosis category in the identified active insurance claim, however, may depend upon what type of information is being aggregated by the data aggregation module 105. In connection with the other figures, the primary diagnosis category in the historic insurance claims that is being matched may similarly be the last primary diagnosis category that was provided. In connection with the information that is illustrated in FIG. 17, however, the primary diagnosis category that is being matched in the historic claim information may be the primary diagnosis category that was identified at a time during the course of each historic insurance claim that matches the current age of the identified active insurance claim.

For example, in the example illustrated in FIG. 17, the active insurance claim is 103 days old. Thus, the database query module 103 is configured to identify historic insurance claims that were associated with the same primary diagnosis category at the 103rd day during the course of these historic insurance claims. The database query module 103 may be configured to query the historic insurance claim information 121 in connection with the matching historic insurance claims to determine whether the primary diagnosis category for any matching historic insurance claim change after the matching historic insurance claim exceeded the age of the identified active insurance claim.

The results of this query may be provided to the data aggregation module 105 which may aggregate the results which may be included in a report by the report generation module 115. As illustrated in FIG. 17, the aggregate of this information indicates that the primary diagnosis category of 28 of the 30 matching historic insurance claims did not subsequently change, while the primary diagnosis category of two of the matching historic insurance claims did. This type of aggregate information can further assist in the determination of the likely outcome of the identified active insurance claim. As illustrated in FIG. 17, other diagnosis information about the matching historic insurance claims may be presented, further assisting in this process.

The active insurance claim analysis system and each of its modules is implemented with a computer system configured to perform the functions that have been described herein for the system and each of its component modules. Each computer system includes one or more processors, memory devices (e.g., random access memories (RAMs), read-only memories (ROMs), and/or programmable read only memories (PROMS)), tangible storage devices (e.g., hard disk drives, CD/DVD drives, and/or flash memories), system buses, video processing components, network communication components, input/output ports, and/or user interface devices (e.g., keyboards, pointing devices, displays, microphones, sound reproduction systems, and/or touch screens). The database 117 is similarly stored in one or more tangible storage devices, such as one or more hard disk drives, CD/DVD drives, and/or flash memories.

The computer system may include one or more computers at the same or different locations. When at different locations, the computers may be configured to communicate with one another through a wired and/or wireless network communication system.

The computer system may include software (e.g., one or more operating systems, device drivers, application programs, and/or communication programs). When software is included, the software includes programming instructions and may include associated data and libraries. When included, the programming instructions are configured to implement one or more algorithms that implement one more of the functions of the computer system, as recited herein. Each function that is performed by an algorithm also constitutes a description of the algorithm. The software may be stored on one or more non-transitory, tangible storage devices, such as one or more hard disk drives, CDs, DVDs, and/or flash memories. The software may be in source code and/or object code format. Associated data may be stored in any type of volatile and/or non-volatile memory.

The components, steps, features, objects, benefits and advantages that have been discussed are merely illustrative. None of them, nor the discussions relating to them, are intended to limit the scope of protection in any way. Numerous other embodiments are also contemplated. These include embodiments that have fewer, additional, and/or different components, steps, features, objects, benefits and advantages. These also include embodiments in which the components and/or steps are arranged and/or ordered differently.

For example, additional variations that may aid in determining probable claim outcome, such as predictive modeling based on the same search criteria, may be incorporated into the product to increase the accuracy.

Unless otherwise stated, all measurements, values, ratings, positions, magnitudes, sizes, and other specifications that are set forth in this specification, including in the claims that follow, are approximate, not exact. They are intended to have a reasonable range that is consistent with the functions to which they relate and with what is customary in the art to which they pertain.

All articles, patents, patent applications, and other publications that have been cited in this disclosure are incorporated herein by reference.

The phrase "means for" when used in a claim is intended to and should be interpreted to embrace the corresponding structures and materials that have been described and their equivalents. Similarly, the phrase "step for" when used in a claim is intended to and should be interpreted to embrace the corresponding acts that have been described and their equivalents. The absence of these phrases in a claim mean that the claim is not intended to and should not be interpreted to be limited to any of the corresponding structures, materials, or acts or to their equivalents.

The scope of protection is limited solely by the claims that now follow. That scope is intended and should be interpreted to be as broad as is consistent with the ordinary meaning of the language that is used in the claims when interpreted in light of this specification and the prosecution history that follows and to encompass all structural and functional equivalents. Notwithstanding, none of the claims are intended to embrace subject matter that fails to satisfy the requirement of Sections 101, 102, or 101 of the Patent Act, nor should they be interpreted in such a way. Any unintended embracement of such subject matter is hereby disclaimed.

Except as stated immediately above, nothing that has been stated or illustrated is intended or should be interpreted to cause a dedication of any component, step, feature, object, benefit, advantage, or equivalent to the public, regardless of whether it is or is not recited in the claims.

The terms and expressions used herein have the ordinary meaning accorded to such terms and expressions in their respective areas, except where specific meanings have been set forth. Relational terms such as first and second and the like may be used solely to distinguish one entity or action from another, without necessarily requiring or implying any actual relationship or order between them. The terms "comprises," "comprising," and any other variation thereof when used in connection with a list of elements in the specification or claims are intended to indicate that the list is not exclusive and that other elements may be included. Similarly, an element proceeded by "a" or "an" does not, without further constraints, preclude the existence of additional elements of the identical type.

The Abstract is provided to help the reader quickly ascertain the nature of the technical disclosure. It is submitted with the understanding that it will not be used to interpret or limit the scope or meaning of the claims. In addition, various features in the foregoing Detailed Description are grouped together in various embodiments to streamline the disclosure. This method of disclosure is not to be interpreted as requiring that the claimed embodiments require more features than are expressly recited in each claim. Rather, as the following claims reflect, inventive subject matter lies in less than all features of a single disclosed embodiment. Thus, the following claims are hereby incorporated into the Detailed Description, with each claim standing on its own as separately claimed subject matter.

The invention claimed is:

1. An insurance claim analysis system for generating information indicative of an outcome of an active insurance claim comprising:
   a historic insurance claim information database configured to hold historic information about historic insurance claims;
   a database query module that has one or more processors configured to query the historic insurance claim information database for historic insurance claims that match search criteria indicative of one or more aspects of the active insurance claim;
   a data aggregation module that has one or more processors configured to calculate an aggregate of an aspect of the historic information about the historic insurance claims that match the search criteria or a subset thereof; and
   a report generation module that has one or more processors configured to generate a report that includes the calculated aggregate of the aspect of the historic information wherein
      the historic information about each historic insurance claim includes information indicative of the payment made for medical services that were provided in connection with the historic insurance claim and the type of that medical services, and the calculated aggregate of an aspect of the historic information is an average of the total payments made for a medical service of each type in connection with the historic insurance claims that match the search criteria; or
      the historic information about each historic insurance claim includes a number of disability days; the calculated aggregate of an assert of the historic information is an average of the number of disability days for the historic insurance claims that match the search criteria; the historic information about some of the historic insurance claims includes one or more co-morbidity factors, each indicative of a complicating medical factor relating to the historic insurance claim; and the calculated aggregate of an aspect of the historic information includes: an average of the number of disability days for the historic insurance claims that match search criteria that includes at least one co-morbidity factor indicative of a complicating medical factor relating to the active insurance claim; and an average of the number of disability days for the historic insurance claims that match search criteria that does not include any co-morbidity factor indicative of a complicating medical factor relating to the active insurance claim.

2. The insurance claim analysis system of claim 1 further comprising:
   a query formulation module that automatically formulates the search criteria; and
   a user interface configured to allow a user to modify at least a portion of the search criteria automatically formulated by the query formulation module.

3. The insurance claim analysis system of claim 2 wherein the user interface is configured to allow a user to modify at least a portion of the search criteria by adding one or more "what if" criteria to the search query to include as search criteria one or more occurrences that might take place in connection with the active insurance claim.

4. The insurance claim analysis system of claim 1:
   further comprising a user interface configured to allow a user to identify a subset of the historic insurance claims that match the search criteria; and
   wherein the search criteria includes criteria limiting the search to the identified subset of the historic insurance claims.

5. The insurance claim analysis system of claim 1 wherein:
   the historic insurance claim information for each historic insurance claim includes a primary diagnosis category indicative of a related group of diagnoses, one of which has been identified as being primarily responsible for the outcome of the historic insurance claim; and
   the search criteria includes a primary diagnosis category indicative of a related group of diagnoses, one of which has been identified as being primarily responsible for the outcome of the active insurance claim.

6. The insurance claim analysis system of claim 5 wherein:
   there are multiple ways of determining which diagnosis is primarily responsible for the outcome of the active insurance claim;
   the insurance claim analysis system further comprises a user interface configured to allow a user to select one of these multiple ways; and
   the primary diagnosis category included with the search criteria is the one that includes the diagnosis determined to be primarily responsible for the outcome of the active insurance claim based on the way selected through the user interface.

7. The insurance claim analysis system of claim 1 wherein:
   the historic information about some of the historic insurance claims includes one or more co-morbidity factors, each indicative of a complicating medical factor relating to the historic insurance claim; and
   the search criteria includes at least one co-morbidity factor indicative of a complicating medical factor relating to the active insurance claim.

8. The insurance claim analysis system of claim 7 wherein the at least one co-morbidity factor is an inflammatory condition and the search criteria formulated by the query formulation module includes this co-morbidity factor.

9. The insurance claim analysis system of claim 7 wherein the at least one co-morbidity factor is a degenerative condition and the search criteria formulated by the query formulation module includes this co-morbidity factor.

10. The insurance claim analysis system of claim 1 wherein:
the historic information about each historic insurance claim includes an amount of money paid for one or more aspects of the historic insurance claim; and
the calculated aggregate of an aspect of the historic information is an average and/or ranked percentiles of money paid on the one or more aspects of the historic insurance claims that match the search criteria or a subset thereof.

11. The insurance claim analysis system of claim 10 wherein:
the data aggregation module is configured to break down the historic insurance claims that match the search criteria into sub-sets based on the amount of money that was paid on an aspect of the historic insurance claims; and
the calculated aggregate of an aspect of the historic information is an average and/or ranked into percentiles amount of money paid on the aspect of the historic insurance claims for each of the sub-sets.

12. The insurance claim analysis system of claim 10 wherein the calculated aggregate of an aspect of the historic information includes multiple percentages, each percentage being associated with an amount of money, and each percentage indicative of the percentage of claims that match the search criteria or a subset thereof that paid the associated amount of money or less.

13. The insurance claim analysis system of claim 1 wherein:
the historic information about each historic insurance claim includes information indicative of medical services that were provided in connection with the historic insurance claim and the type of that medical services; and
the calculated aggregate of an aspect of the historic information is an average of the number of times a medical service of each type was sought in connection with the historic insurance claims that match the search criteria.

14. The insurance claim analysis system of claim 1 wherein:
the historic information about each historic insurance claim includes information indicative of the payment made for medical services that were provided in connection with the historic insurance claim and the type of that medical services; and
the calculated aggregate of an aspect of the historic information is an average of the total payments made for a medical service of each type in connection with the historic insurance claims that match the search criteria.

15. The insurance claim analysis system of claim 1 wherein:
the historic information about each historic insurance claim includes a number of disability days; and
the calculated aggregate of an aspect of the historic information is an average of the number of disability days for the historic insurance claims that match the search criteria.

16. The insurance claim analysis system of claim 15 wherein:
the historic information about some of the historic insurance claims includes one or more co-morbidity factors, each indicative of a complicating medical factor relating to the historic insurance claim; and
the calculated aggregate of an aspect of the historic information includes:
an average of the number of disability days for the historic insurance claims that match search criteria that includes at least one co-morbidity factor indicative of a complicating medical factor relating to the active insurance claim; and
an average of the number of disability days for the historic insurance claims that match search criteria that does not include any co-morbidity factor indicative of a complicating medical factor relating to the active insurance claim.

17. The insurance claim analysis system of claim 1 wherein:
the historic information about each of some of the historic insurance claims includes information indicative of a change during the course of the historic insurance claim in a primary diagnosis category that has been identified as being primarily responsible for the historic insurance claim outcome; and
the calculated aggregate of an aspect of the historic information is an aggregate of the number of the historic insurance claims that match the search criteria and that have an outcome indicative of no change during the course of the historic insurance claim in a primary diagnosis category.

18. The insurance claim analysis system of claim 1 wherein the data aggregation module is configured to calculate aggregates of multiple aspects of the historic information, each about the historic claims that match the search criteria or a portion thereof.

19. The insurance claim analysis system of claim 1 further comprising a sentinel event notification module that monitors information about active insurance claims and issues an alert to one or more persons each time the information about the active insurance claims indicates the occurrence of a sentinel event that is likely to have a significant effect on the outcome of one of the active insurance claims.

20. Non-transitory, tangible, computer-readable media containing a program of computer instructions configured to implement the following process for generating information indicative of an outcome of an active insurance claim when run in a computer system:
querying a historic insurance claim information database that holds historic information about historic insurance claims for historic insurance claims that match search criteria indicative of one or more aspects of the active insurance claim;
calculating an aggregate of an aspect of the historic information about the historic insurance claims that match the search criteria or a subset thereof; and
generating a report that includes the calculated aggregate of the aspect of the historic information,
wherein:
the historic information about each historic insurance claim includes information indicative of the payment made for medical services that were provided in connection with the historic insurance claim and the type of that medical services, and the calculated aggregate of an aspect of the historic information is an average of the total payments made for a medical service of each type in connection with the historic insurance claims that match the search criteria; or
the historic information about each historic insurance claim includes a number of disability days; the calculated aggregate of an aspect of the historic information is an average of the number of disability days for the historic insurance claims that match the search criteria; the historic information about some of the historic insurance claims includes one or more co-morbidity factors, each indicative of a complicating medical factor relating to the historic insurance claim; and the calculated aggregate of an aspect of the historic information includes: an average of the number of disability days for the historic insurance claims that match search criteria that includes at least one co-morbidity factor indicative of a complicating medical factor relating to the active insurance claim; and an average of the number of disability days for the historic insurance claims that match search criteria that does not include any co-morbidity factor indicative of a complicating medical factor relating to the active insurance claim.

\* \* \* \* \*